United States Patent [19]

Wade

[11] 4,332,812
[45] Jun. 1, 1982

[54] ANTIINFLAMMATORY CARBINOLAMINE ESTERS OF 1,2,4-TRIAZOLES

[75] Inventor: Peter C. Wade, Pennington, N.J.

[73] Assignee: E. R. Squibb & Sons, Inc., Princeton, N.J.

[21] Appl. No.: 194,186

[22] Filed: Oct. 6, 1980

[51] Int. Cl.$^3$ .................... A61K 31/41; C07D 249/08
[52] U.S. Cl. ..................................... 424/269; 548/262
[58] Field of Search .................... 548/262; 424/269

[56] References Cited

U.S. PATENT DOCUMENTS

| 4,006,159 | 2/1977 | Newman . |
| 4,154,841 | 5/1979 | Wade et al. . |
| 4,169,148 | 9/1979 | Wade et al. . |

FOREIGN PATENT DOCUMENTS

| 2640823 | 3/1977 | Fed. Rep. of Germany ...... 548/262 |
| 67130 | 6/1969 | German Democratic Rep. . |
| 7406067 | 11/1974 | Netherlands ........................ 424/269 |
| 1351430 | 5/1974 | United Kingdom . |

OTHER PUBLICATIONS

"A Novel Synthesis for 3-Substituted 1,2,4—Triazoles," Journal für praktische Chemie, vol. 311, 1969, pp. 477–489, Becker et al.

"Reactions of Aromatic Amide Carbamylhydrazones with Acetic Anhydride," Ikizler et al., Chem. Abstracts, vol. 86, Abstract No. 55351w (1977).

*Primary Examiner*—Alton D. Rollins
*Attorney, Agent, or Firm*—Lawrence S. Levinson; Burton Rodney

[57] ABSTRACT

Carbinolamine esters of 1,2,4-triazoles are provided having the structure

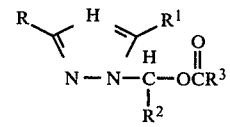

wherein R, R$^1$, R$^2$ and R$^3$ are as defined herein. These compounds are useful as antiinflammatory agents.

11 Claims, No Drawings

ANTIINFLAMMATORY CARBINOLAMINE ESTERS OF 1,2,4-TRIAZOLES

BACKGROUND OF THE INVENTION

East German Pat. No. 67,130 to Becker et al. describes a procedure for the synthesis of 3,5-disubstituted-1,2,4-triazoles useful as intermediates. The product triazoles are formed as follows. A starting material of structure I

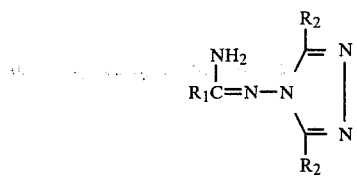

wherein $R_1$ is alkyl, aryl, aralkyl, alkoxyalkyl, acylaminoalkyl, or a heterocyclic group and $R_2$ is hydrogen, alkyl, or aryl, is treated with acylating agent, such as an acid chloride or acid anhydride or an alkylating agent, such as an alkylhalide. Depending on conditions, the product is isolated directly (or as its salt) or an intermediate product or residue of undefined structure or composition is first isolated and then converted to the triazole product by thermolysis or hydrolysis. A by-product is described in several examples which is a diacyl (or dialkyl) hydrazine presumably arising from the 1,2-hydrazino portion of the starting thiazole that is lost in the course of the reaction.

In Example 10 of the Becker et al. patent, N-4-(3,5-dimethyl-1,2,4-triazolyl)benzamidine is reacted with acetic anhydride at 170° C. for 2-3 hours with evaporation of the volatile materials to form a residue ("Rückstand") of unknown composition and utility. The residue is heated for 3 hours in water to give the 3-methyl-5-phenyl-1,2,4-triazole product.

Becker et al neither identify the components of the residue nor separate out or isolate such components. However, it is believed that about one-half of the Rückstand or residue is a mixture of various by-products, and the remainder is a mixture of 1-acetyl-5-methyl-3-phenyl-1H-1,2,4-triazole and 1-acetyl-3-methyl-5-phenyl-1H-1,2,4-triazole in about a 90:10 ratio to each other.

Becker et al. in a paper entitled "A Novel Synthesis for 3-Substituted 1,2,4-Triazoles," *Journal fur praktische Chemie*. Volume 311, 1969, pages 477–489, disclose the preparation of 3-substituted-1,2,4-triazoles including 3-phenyl-1,2,4-triazoles of the structure

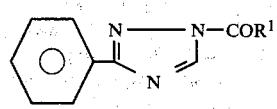

wherein $R^1$ can be ethoxy, methyl, ethyl or n-propyl. A general preparation for 1-acetyl-3-phenyl-1,2,4-triazole and 1-propionyl-3-phenyl-1,2,4-triazole is set out on page 487.

U.S. Pat. No. 4,006,159 to Newman discloses mixtures of acyl-substituted 1,2,4-triazole-3-carboxamides which may be presented by the following structural formulae:

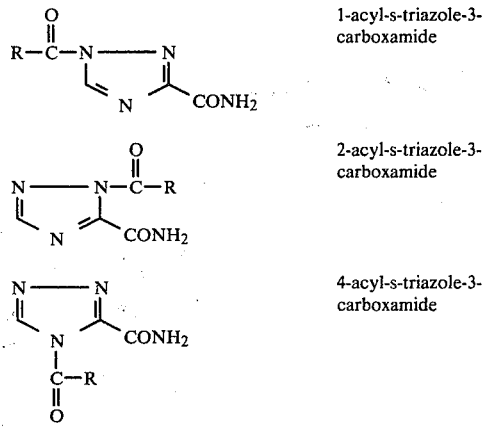

wherein each mixture consists of all three forms wherein R is the same in each form and wherein R is hydrogen, alkyl having up to 15 carbon atoms; cycloalkyl having from 3 to 8 carbon atoms; phenyl; ortho-, meta-, or para-hydroxyphenyl; ortho-, meta-, or paramethoxyphenyl; or adamantyl. The above mixture is said to be useful as anti-viral agents.

Ikizler et al Chem. Abstracts, Vol. 86, Abstract No. 55351w (1977) discloses the preparation of triazoles of the structure

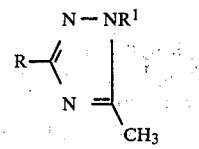

wherein $R^1$ is acetyl, and R is 4-$CH_3C_6H_4$, 3-$O_2NC_6H_4$- or 2-naphthyl. No utility is given for such compounds.

British Specification No. 1,351,430 discloses triazoles of the formula

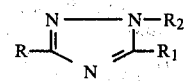

wherein R and $R_1$ are phenyl or substituted phenyl though not both simultaneously phenyl, and $R_2$ is hydrogen or $C_1$–$C_4$ alkyl, which are said to be useful as CNS depressants.

U.S. Pat. No. 4,169,148 discloses a method of treating inflammatory and/or psychotic conditions with derivatives of 1,2,4-triazoles having the structure

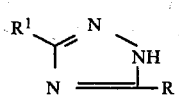

wherein R and $R^1$ may be the same or different and may be lower alkyl, cycloalkyl, cycloalkyl-lower alkyl, phenyl or phenyl-lower alkyl. Where present, the phenyl whether alone or as part of a lower alkyl group may be substituted with one or two of halogen, trifluoromethyl, lower alkyl, lower alkoxy or lower alkylthio.

U.S. Pat. No. 4,154,841 discloses 1-acyl-3(5)-alkyl-5(3)-phenyl-1,2,4-triazoles which are useful as antiinflammatory agents and have the structure

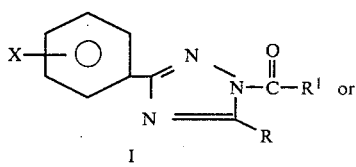

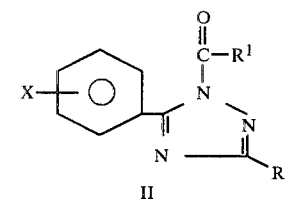

wherein R is lower alkyl or cycloalkyl, R¹ is lower alkyl or cycloalkyl, and X is hydrogen, halogen, lower alkyl, lower alkoxy, nitro or trifluoromethyl.

The carbinolamine esters of 1,2,4-triazoles of the invention which are useful as antiinflammatory agents have the structure

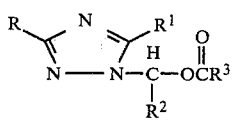

wherein
- R is lower alkyl, cycloalkyl, cycloalkyl-lower alkyl, phenyl or phenyl-lower alkyl. The phenyl may be substituted with one or two halogen, trifluoromethyl, lower alkyl, lower alkoxy or lower alkylthio groups.
- R¹ may be lower alkyl, phenyl-lower alkyl, cycloalkyl or cycloalkyl-lower alkyl;
- R² may be hydrogen, lower alkyl, cycloalkyl, phenyl or phenyl substituted with any of the above substituents; and
- R³ may be lower alkyl, cycloalkyl, phenyl or phenyl substituted with any of the above substituents.

The preferred compounds of the invention are those of formula I wherein R¹, R² and R³ are lower alkyl and R is phenyl or substituted phenyl.

The term "lower alkyl" as used herein refers to alkyl groups having 1 to 7 carbons, preferably 1 to 4 carbons, including straight or branched chain groups, such as methyl, ethyl, n-propyl, i-propyl, 2-propylbutyl, n-butyl, s-butyl, i-butyl, t-butyl, n-pentyl, n-hexyl, and n-heptyl and the various branched chain isomers thereof.

The terms "lower alkoxy" and "lower alkylthio" as used herein refers to lower alkyl groups as defined above attached to an oxygen atom or sulfur atom, respectively, with methoxy being preferred.

The term "cycloalkyl" as used herein refers to saturated carbocyclic radicals containing 3 to 7 carbons in the ring, such as cyclopropyl, cyclobutyl, cyclopentyl, cyclohexyl or cycloheptyl.

The term "halogen" as employed herein refers to chlorine, bromine, iodine or fluorine with chlorine and bromine being preferred.

The compounds of formula I of the invention may be prepared by sequentially treating a 1,2,4-triazole of the structure

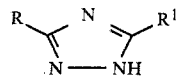

(prepared as described in U.S. Pat. No. 4,169,148) with an organic base, such as a tertiary amine, for example, triethylamine or N-methylmorpholine, treating the mixture with an aldehyde of the structure

and then finally treating the reaction mixture with an acylating agent of the structure

wherein X is Cl or Br, in the presence of an inert solvent, such as 1,2-dimethoxyethane, ether, tetrahydrofuran, dioxane, toluene and the like, to form compounds of formula I.

The compounds of formula I have antiinflammatory activity as measured by the mouse active arthus (MAA) test and/or other related tests and are useful as antiinflammatory agents and may be used, for example, in a manner similar to phenylbutazone or indomethacin. They may be used to decrease joint swelling, tenderness, pain and stiffness in mammalian species, e.g., in conditions such as rheumatoid arthritis. The quantity administered ranges from about 1 mg to about 150 mg per kg and preferably from about 5 mg to about 75 mg per kg of body weight per day.

A compound of formula I can be administered orally or parenterally (for example, intraperitoneally, subcutaneously, intramuscularly or intravenously). Powders can be prepared by comminuting the active ingredient with a similarly comminuted diluent, such as starch or lactose. Suitable forms for oral administration include capsules, tablets, troches, elixirs, wafer, chewing gum, syrups, and a suitable form for parenteral administration is a sterile injectable. Such unit dosage forms are prepared by compounding with a conventional vehicle, excipients, binders, preservatives, stabilizers, flavoring agents or the like as called for by acceptable pharmaceutical practice. Also, the compounds used in this invention can be formulated with other pharmaceutically active compounds.

The tablets, troches, pills, capsules and the like may also contain the following: a binder, such as gum tragacanth, acacia, corn starch or gelatin; an excipient, such as dicalcium phosphate, a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen or cherry flavoring. When the dosage unit form is a capsule, it may contain in addition to materials of the above type a liquid carrier, such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring, such as cherry or orange flavor. Of course, any material used in preparing any dosage unit form should be pharmaceutically pure and substantially non-toxic in the amounts employed.

The following examples are illustrative of the invention and represent preferred embodiments. Other modifications may be readily produced by suitable variations of the reactions. All temperatures are on the centigrade scale.

EXAMPLE 1

3-(4-Chlorophenyl)-α,5-dimethyl-1H-1,2,4-triazole-1-methanol, acetate ester

To a stirring solution of 1.8 g (9.3 mmole) of 3-(4-chlorophenyl)-5-methyl-1,2,4-triazole (prepared as described in U.S. Pat. No. 4,169,148) and 2.0 g (19.8 mmole) of triethylamine in 30 ml of 1,2-dimethoxyethane is added 1.2 g (27 mmole) of acetaldehyde dropwise. After 30 minutes 1.0 g (13 mmole) of acetyl chloride is added dropwise. After stirring 30 minutes, the mixture is filtered, evaporated to dryness and chromatographed on silica gel with ether. The first compound eluted is the N-acetyl derivative, that is, 1-acetyl-3-(4-chlorophenyl)-5-methyl-1H-1,2,4-triazole. The second major compound eluted is the title product. The fractions containing the product are stripped to yield 1.4 g (54%) which is taken up in 1 ml of acetonitrile and allowed to stand overnight. The resulting crystals (1.0 g) are filtered off and dried under vacuum, m.p. 101.5°–103°.

EXAMPLES 2 TO 16

Following the procedure of Example 1, but substituting for 3-(4-chlorophenyl)-5-methyl-1,2,4-triazole, the compound shown in Column I of Table A below which compound is prepared as described in U.S. Pat. No. 4,169,148 (Examples 2 to 16 thereof), substituting for the acetaldehyde, the aldehyde shown in Column II, and substituting for the acetyl chloride, the compound shown in Column III, the compound of the invention shown in Column IV is obtained.

TABLE A

| Ex. No. | Column I R | Column I $R^1$ | Column II $HCR^2$ $R^2$ | Column III $ClCR^3$ $R^3$ | Column IV R | $R^1$ | $R^2$ | $R^3$ |
|---|---|---|---|---|---|---|---|---|
| 2. | (thienyl) | (phenyl) | H | $CH_3$ | as in Column I | as in Col. II | as in Col. III | |
| 3. | $CH_3$ | $CH_3$ | $CH_3$ | $C_6H_5$ | | | | |
| 4. | $C_6H_4CH_2-$ | $C_2H_5$ | (thienyl) | $CH_3$ | | | | |
| 5. | $C_6H_5$ | $-CH_2-$(thienyl) | $C_6H_5$ | $CH_3$ | | | | |
| 6. | p-$CH_3O-C_6H_4CH_2$ | $C_2H_5$ | p-$CH_3-C_6H_4$ | $C_2H_5$ | | | | |
| 7. | $C_6H_5$ | $C_2H_5$ | H | (thienyl) | | | | |
| 8. | p-$Cl-C_6H_4$ | $CH_3$ | $C_2H_5$ | $C_6H_5$ | | | | |
| 9. | p-$CF_3-C_6H_4-$ | (thienyl) | (phenyl) | $CH_2C_6H_5$ | | | | |
| 10. | 2,6-diCl-$C_6H_3$ | $CH_3$ | $C_6H_5$ | $C_6H_5$ | | | | |
| 11. | $C_6H_5$ | $C_2H_5$ | m-$C_2H_5O-C_6H_4$ | $CH(C_3H_7)_2$ | | | | |
| 12. | m-$C_2H_5OC_6H_4$ | n-$C_4H_9$ | p-$CH_3S-C_6H_4$ | $CH_3$ | | | | |
| 13. | p-$C_2H_5-C_6H_4$ | $C_2H_5$ | p-$Cl-C_6H_4$ | $C_2H_5$ | | | | |
| 14. | (thienyl)-$CH_2$ | (thienyl)-$CH_2$ | p-$CF_3-C_6H_4$ | (thienyl) | | | | |
| 15. | $C_6H_5$ | (phenyl)-$(CH_2)_2$ | $C_6H_5CH_2$ | p-$Cl-C_6H_4-$ | | | | |
| 16. | p-$CH_3S-C_6H_4-$ | (thienyl) | $C_3H_7$ | p-$CH_3-C_6H_4-$ | | | | |

EXAMPLE 17

Alternate Procedure for Preparing 3-(4-Chlorophenyl)-α,5-dimethyl-1H-1,2,4-triazole-1-methanol, Acetate Ester To a suspension of 0.2 g (5.3 mmol) of deactivated LiAlH$_4$ in 20 ml of ester is added, all at once, 0.5 g (2 mmol) of 1-acetyl-3-(4-chlorophenyl)-5-methyl-1H-1,2,4-triazole (prepared as described in U.S. Pat. No. 4,169,148). The resulting mixture (both components not completely soluble) is allowed to stir overnight. TLC of the mixture (spotted directly) on silica gel developed with 3:2 chloroform: ethyl acetate shows the starting triazole ($R_f$ 0.91) as a minor but significant spot, the title compound ($R_f$ 0.63) and 3-(4-chlorophenyl)-5-methyl- 1H-1,2,4-triazole ($R_f$ 0.19). An aliquot of the reaction mixture is worked up by adding 10% NaOH and shaking. TLC of the ether layer (3:2 chloroform: ethyl acetate) shows only spots corresponding to the starting triazole and the title compound. The reaction mixture is diluted to 50 ml with ether, treated cautiously with excess 10% NaOH and the aqueous layer extracted 3 times with ether. The ether portions are combined, dried ($Na_2SO_4$) and evaporated in vacuo to yield an oil. The oil is chromatographed on 3 preparative plates (Quantum, PLQF 1000) with 3:2 chloroform: ethyl acetate. The plates are sprayed with methanol and the bands corresponding to the title compound scraped off and extracted with chloroform. The solvent is removed in vacuo and the residue taken up in 1 ml of acetonitrile which is allowed to evaporate slowly to yield 200 mg (36%) of the title compound: m.p. 101°–3° C.

EXAMPLE 18

Parenteral Composition Containing 3-(4-Chlorophenyl)-α,5-dimethyl-1H-1,2,4-triazole-1-methanol, acetate ester A dispersion suitable for parenteral administration is prepared by dispersing 1 mg of 3-(4-chlorophenyl)-α,5-dimethyl-1H-1,2,4-triazole-1-methanol, acetate ester in about 100 ml of water for injection.

EXAMPLE 19

Tablets Containing 3-(4-chlorophenyl)-α,5-dimethyl-1H-1,2,4-triazole-1-methanol, acetate ester The following ingredients are used to make 1,000 200 mg tablets each containing 100 mg of active ingredient:

| | |
|---|---|
| 3-(4-chlorophenyl-α,5-dimethyl-1H-1,2,4-triazole-1-methanol, acetate ester | 100 gm |
| Polyvinyl pyrrolidone | 7.5 gm |
| Lactose | 20 gm |
| Magnesium stearate | 3.5 gm |
| Corn starch | 17.5 gm |
| Avicel (microcrystalline cellulose) | 51.5 gm |

The medicament and lactose are thoroughly admixed, the polyvinyl pyrrolidone is dissolved in ethanol USP to make a 30% solution. This solution is used to granulate the mixture of medicament and lactose. The granulation is passed through a No. 16 screen and air dried. The dried granulation is then passed through a No. 20 screen. To the screened granulate are added the magnesium stearate, Avicel and the corn starch and the mixture is blended. The blend is then compressed into 200 mg tablets on a standard concave punch. The tablets are then veneer coated with methyl cellulose in a spray gun.

What is claimed is:

1. A compound of the structure

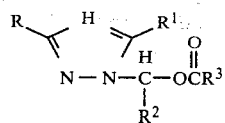

wherein

R is lower alkyl, cycloalkyl, cycloalkyl-lower alkyl, phenyl, phenyl-lower alkyl or phenyl substituted with halogen, $CF_3$, lower alkyl, lower alkoxy or lower alkylthio, $R^1$ is lower alkyl, cycloalkyl or cycloalkyl-lower alkyl, $R^2$ is H, lower alkyl, cycloalkyl, phenyl or phenyl substituted with halogen, $CF_3$, lower alkyl, lower alkoxy or lower alkylthio, and $R^3$ is lower alkyl, cycloalkyl, phenyl or phenyl substituted with halogen, $CF_3$, lower alkyl, lower alkoxy or lower alkylthio, provided that where $R^3$ is lower alkyl R is other than lower alkyl.

2. The compound of claim 1 wherein R is phenyl or substituted phenyl.

3. The compound of claim 1 wherein $R^1$, $R^2$ and $R^3$ are lower alkyl.

4. The compound of claim 1 wherein R is phenyl or substituted phenyl and $R^1$, $R^2$ and $R^3$ are lower alkyl.

5. The compound of claim 4 wherein R is halogen substituted phenyl and $R^1$, $R^2$ and $R^3$ are each methyl or ethyl.

6. The compound as defined in claim 1 having the name 3-(4-chlorophenyl)-α,5-dimethyl-1H-1,2,4-triazole-1-methanol, acetate ester.

7. An anti-inflammatory composition which comprises an anti-inflammatory amount of a compound as defined in claim 1 and a pharmaceutically acceptable carrier therefor.

8. The composition as defined in claim 7 wherein the compound has the name 3-(4-chlorophenyl)-α,5-dimethyl-1H-1,2,4-triazole-1-methanol, acetate ester.

9. A method for treating an inflammatory condition in a mammalian host, which comprises administering an effective amount of a compound as defined in claim 1.

10. The method as defined in claim 9 wherein the compound is employed in conjunction with a physiologically acceptable carrier.

11. The method as defined in claim 9 wherein said compound has the name 3-(4-chlorophenyl)-α,5-dimethyl-1-methanol, acetate ester.

* * * * *

UNITED STATES PATENT AND TRADEMARK OFFICE
CERTIFICATE OF CORRECTION

PATENT NO. : 4,332,812
DATED : June 1, 1982
INVENTOR(S) : Peter C. Wade

It is certified that error appears in the above—identified patent and that said Letters Patent is hereby corrected as shown below:

On the title page, the structure in the Abstract should read

-- 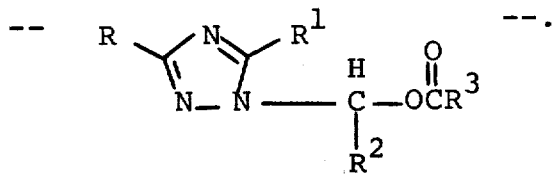 --.

Column 8, the structure in Claim 1 should read

-- 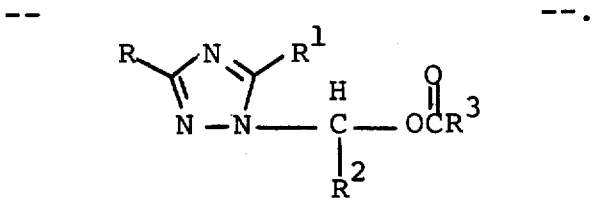 --.

Signed and Sealed this

Seventh Day of September 1982

[SEAL]

Attest:

GERALD J. MOSSINGHOFF

Attesting Officer    Commissioner of Patents and Trademarks